(12) United States Patent
Takegawa et al.

(10) Patent No.: US 10,520,468 B2
(45) Date of Patent: Dec. 31, 2019

(54) INSPECTION APPARATUS FOR GAS SENSOR

(71) Applicant: NGK INSULATORS, LTD., Nagoya-shi, Aichi (JP)

(72) Inventors: Kazuki Takegawa, Tokai (JP); Naoya Saito, Slaskie (PL)

(73) Assignee: NGK INSULATORS, LTD., Nagoya (JP)

( * ) Notice: Subject to any disclaimer, the term of this patent is extended or adjusted under 35 U.S.C. 154(b) by 265 days.

(21) Appl. No.: 15/471,447

(22) Filed: Mar. 28, 2017

(65) Prior Publication Data

US 2017/0284960 A1 Oct. 5, 2017

(30) Foreign Application Priority Data

Mar. 31, 2016 (JP) .................................. 2016-070074

(51) Int. Cl.
*G01N 27/416* (2006.01)
*G01N 27/407* (2006.01)
(Continued)

(52) U.S. Cl.
CPC ..... *G01N 27/4163* (2013.01); *G01N 27/4074* (2013.01); *G01N 27/4077* (2013.01);
(Continued)

(58) Field of Classification Search
CPC ............. G01N 33/007; G01N 33/0006; G01N 2033/0072; G01N 27/4163;
(Continued)

(56) References Cited

U.S. PATENT DOCUMENTS 7,530,255 B2 * 5/2009 Frank ................. G01N 33/0006
73/1.03
8,449,743 B2 5/2013 Sekiya et al.
(Continued)

FOREIGN PATENT DOCUMENTS

DE 102014004618 A1 10/2015
JP 2008-2938 A 1/2008
(Continued)

OTHER PUBLICATIONS

The extended search report for the corresponding European application No. 17000522.7 dated Jul. 11, 2017.

*Primary Examiner* — Maris R Kessel
*Assistant Examiner* — Vivian A Tran
(74) *Attorney, Agent, or Firm* — Global IP Counselors, LLP

(57) ABSTRACT

An inspection apparatus capable of performing responsivity inspection on a plurality of gas sensors at equivalent accuracies is provided. The inspection apparatus includes a plurality of inspected sensor disposing parts that are provided halfway through one gas flow path at equal intervals in an extending direction of the flow path and in each of which a gas sensor to be inspected is disposed, and a plurality of straightening plates provided upstream of each of the inspected sensor disposing parts on the gas flow path and separated at a constant distance from the inspected sensor disposing parts. The straightening plates each include a rectangular opening orthogonal to the gas flow path and open to the gas flow path. When the gas flow path extends in one direction in a horizontal plane, the opening has a longitudinal direction along a direction orthogonal to the one direction in the horizontal plane.

5 Claims, 15 Drawing Sheets

(51) Int. Cl.
   *G01N 27/41*        (2006.01)
   *G01N 33/00*        (2006.01)
   *G01N 27/417*       (2006.01)

(52) U.S. Cl.
   CPC ......... *G01N 27/41* (2013.01); *G01N 27/4175* (2013.01); *G01N 33/007* (2013.01); *G01N 33/0037* (2013.01); *G01N 2033/0072* (2013.01); *Y02A 50/245* (2018.01)

(58) Field of Classification Search
   CPC ........... G01N 27/4074; G01N 27/4077; G01N 27/41; G01N 27/4175; G01N 33/0037; Y02A 50/245
   See application file for complete search history.

(56)               References Cited

U.S. PATENT DOCUMENTS

| | | |
|---|---|---|
| 2009/0095048 A1 | 4/2009 | Sakai et al. |
| 2015/0020569 A1 | 1/2015 | Ostermann et al. |
| 2015/0276695 A1* | 10/2015 | Kaneblei ............ G01N 33/0006 73/1.06 |

FOREIGN PATENT DOCUMENTS

| | | |
|---|---|---|
| JP | 2011-38953 A | 2/2011 |
| JP | 2014-47685 A | 3/2014 |
| JP | 2015-172545 A | 10/2015 |

\* cited by examiner

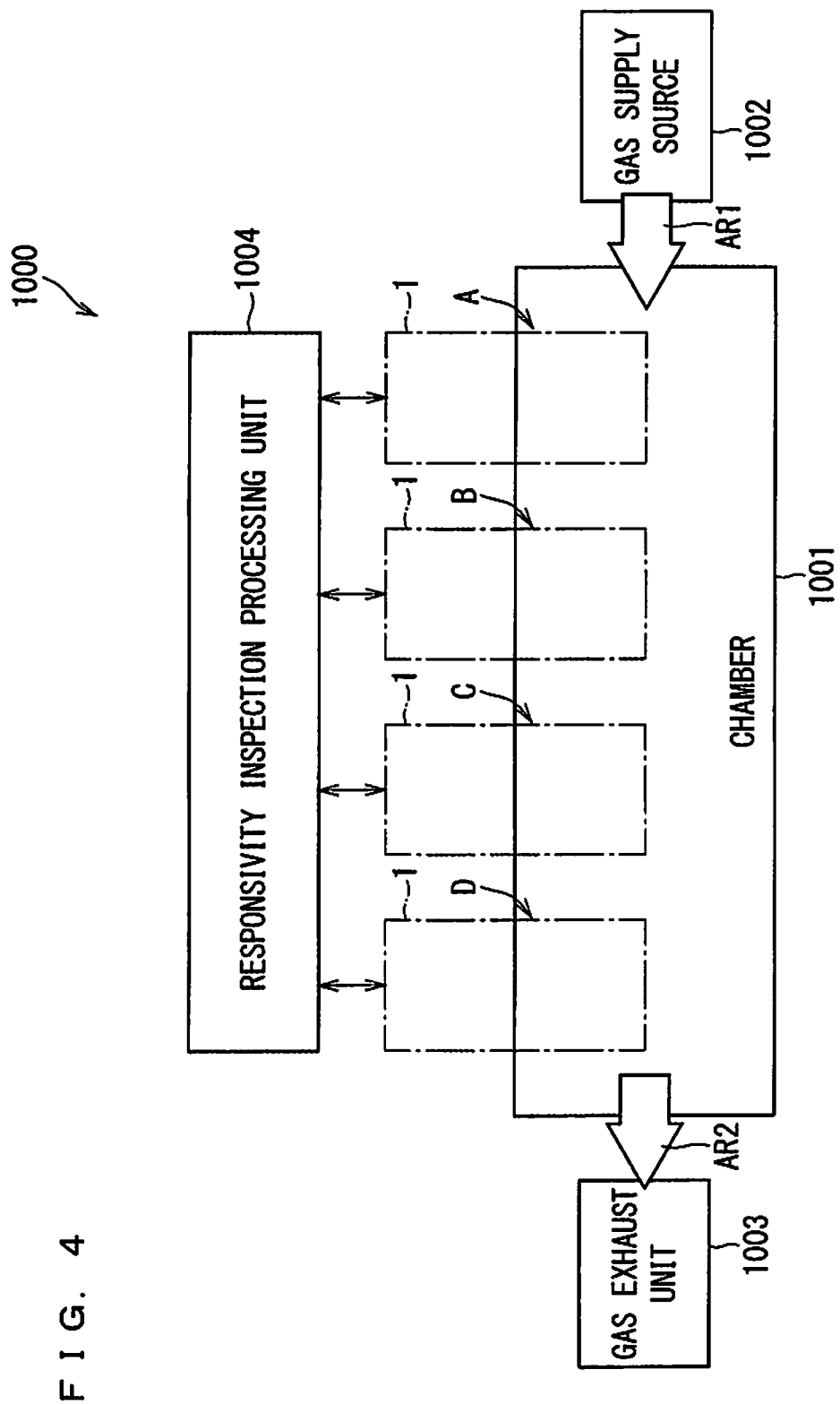
F I G. 4

F I G. 7
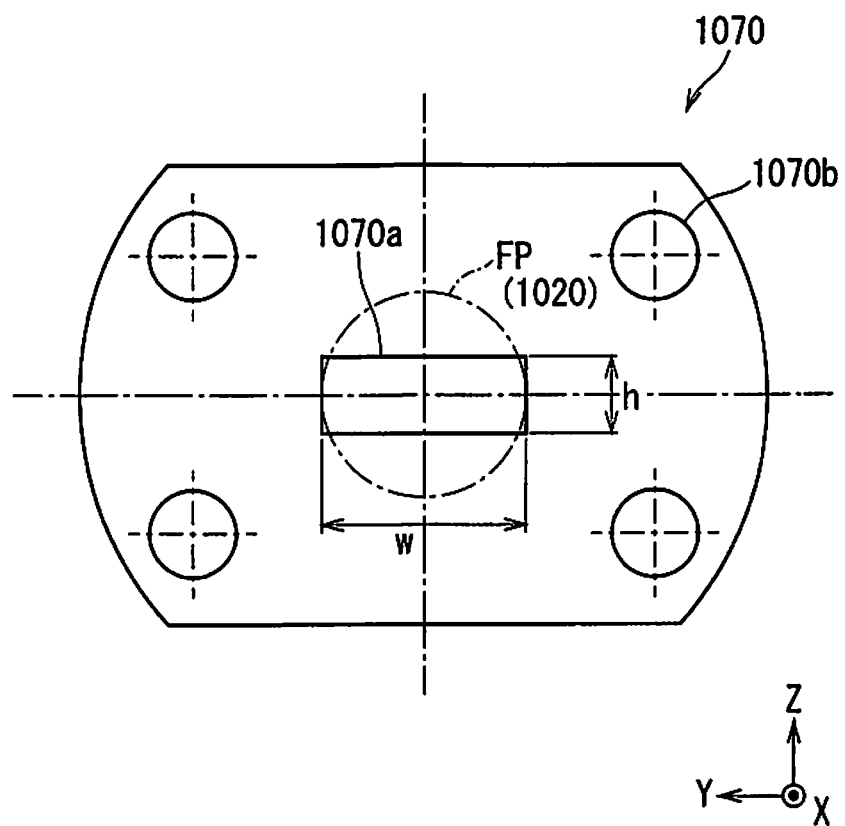

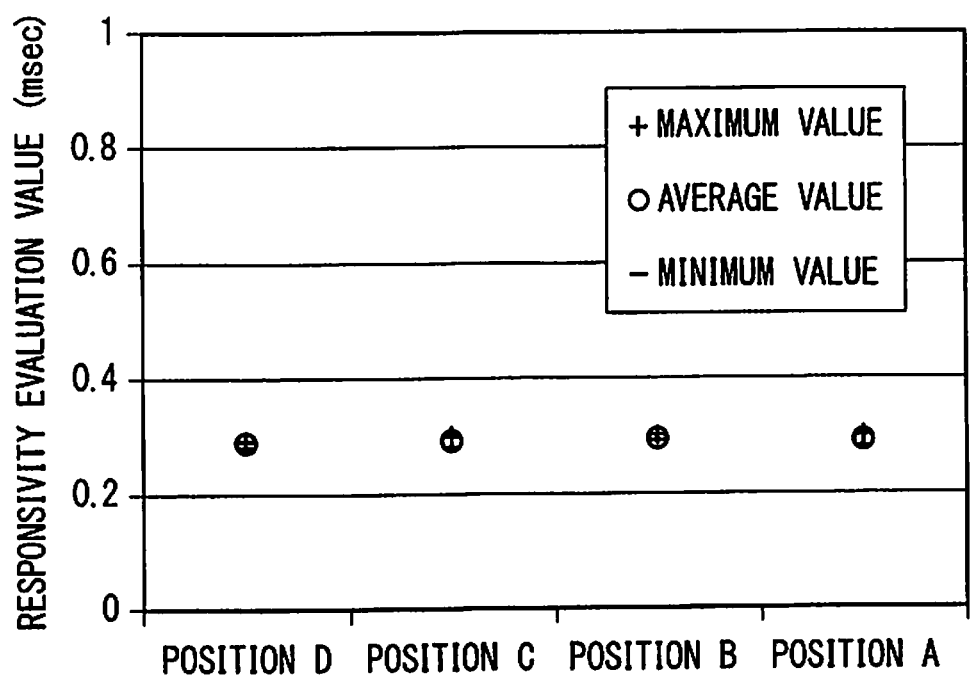
F I G. 1 6

INSPECTION APPARATUS FOR GAS SENSOR

BACKGROUND OF THE INVENTION

Field of the Invention

The present invention relates to an inspection apparatus for a gas sensor, and particularly relates to an apparatus configured to inspect responsivity of the gas sensor.

Description of the Background Art

Conventionally, various kinds of measurement devices have been used to measure the concentration of a desired gas component in a measurement gas. For example, a gas sensor including an electrochemical cell in which an electrode made of, for example, Pt is formed on a solid electrolyte layer having oxygen ion conductivity, such as zirconia ($ZrO_2$), is publicly known as a device configured to measure the concentration of a predetermined gas component in a measurement gas, such as a combustion gas.

Such a gas sensor is used to measure, for example, a desired gas component contained in the exhaust gas of an automobile. A gas sensor attached to an exhaust pipe of an automobile is provided with a protection cover configured to protect a sensor element so as to mainly prevent adhesion of water generated at start of an engine to the sensor element and entrance of water into the sensor element (for example, Japanese Patent Application Laid-Open No. 2011-38953).

Inspection needs to be performed before shipment to check whether an individual manufactured gas sensor has responsivity determined as a standard in advance. The responsivity is one of characteristics used to evaluate the gas sensor, and is expressed, for example, as a time (response time) taken until the gas sensor actually outputs a signal (current value or voltage value) indicating detection of a gas component to be detected after a measurement gas containing the gas component is provided in a space in which the gas sensor is present. A shorter response time indicates that the gas sensor has excellent responsivity.

In a case of the gas sensor provided with the protection cover as described above, whether the gas component to be detected exists in the measurement gas can be determined only after the measurement gas outside of the protection cover reaches a detection electrode (measurement electrode) provided at a predetermined position of the sensor element. Thus, whether the response time is in a predetermined range is an important factor to achieve timely detection of the gas component to be detected.

It is preferable that the measurement (responsivity measurement) for inspecting the responsivity is performed simultaneously on a plurality of gas sensors for improved productivity. This can be achieved by, for example, providing a plurality of measuring ports halfway through one gas flow path and performing the responsivity measurement simultaneously at the measuring ports. However, in light of that this measurement is performed to inspect the responsivity, measurement performed on one gas sensor needs to provide the same result ideally for any measuring port. This requires that the reliability (accuracy) of the responsivity measurement is substantially the same among the measuring ports.

SUMMARY OF THE INVENTION

The present invention relates to a device configured to inspect the responsivity of a gas sensor, and particularly is directed to the configuration thereof.

According to the present invention, an apparatus configured to inspect responsivity of a gas sensor includes: a chamber including one gas flow path; a plurality of inspected sensor disposing parts that are provided halfway through the one gas flow path at equal intervals in an extending direction of the one gas flow path and in each of which a gas sensor to be inspected is disposed; and a plurality of straightening plates provided on positions upstream of each of the inspected sensor disposing parts on the one gas flow path, each of the positions separated at a constant distance from the corresponding inspected sensor disposing parts. The straightening plates each include a rectangular opening orthogonal to the one gas flow path and open to the one gas flow path. When the one gas flow path extends in one direction in a horizontal plane, the opening has a longitudinal direction along a direction orthogonal to the one direction in the horizontal plane. Responsivity of the gas sensor is inspected by causing a gas for inspection to flow through the one gas flow path when the gas sensor to be inspected is disposed at each of the inspected sensor disposing parts.

According to the present invention, in an inspection apparatus provided with a plurality of inspection positions halfway through the one gas flow path and configured to perform responsivity inspection on a plurality of gas sensors, fluctuation of the responsivity evaluation value among the inspection positions can be reduced.

Preferably, the inspection apparatus of a gas sensor according to the present invention further includes: a dummy sensor disposing part provided halfway through the one gas flow path and upstream of an inspected sensor disposing part on a most upstream side among the inspected sensor disposing parts. An interval between the dummy sensor disposing part and the inspected sensor disposing part on the most upstream side is same as an interval between the inspected sensor disposing parts. A straightening plate same as the straightening plates is provided on a position upstream of the dummy sensor disposing part on the one gas flow path, with separated from the dummy sensor disposing part by the constant distance. A dummy sensor having a structure same as a structure of the gas sensor to be inspected is disposed at the dummy sensor disposing part, at least when the responsivity of the gas sensor is inspected.

In this manner, since a dummy pipe unit having a configuration identical to that of an inspection pipe part is provided upstream of the inspection pipe part that provides an inspection position on the most upstream side, the fluctuation of the responsivity evaluation value among the inspection positions can be further reduced.

Thus, it is an objective of the present invention to provide an inspection apparatus capable of simultaneously performing responsivity inspection of a plurality of gas sensors at equivalent accuracies.

These and other objects, features, aspects and advantages of the present invention will become more apparent from the following detailed description of the present invention when taken in conjunction with the accompanying drawings.

BRIEF DESCRIPTION OF THE DRAWINGS

FIG. 4 is a diagram schematically illustrating a configuration of an inspection apparatus 1000 configured to perform the responsivity inspection;

FIG. 7 is a front view of a straightening plate 1070;

FIG. 16 is a diagram showing responsivity evaluation values of the gas sensor 1 disposed at inspection positions A to D, which are obtained by an inspection apparatus according to Example 2;

DESCRIPTION OF THE PREFERRED EMBODIMENTS

<Configuration of Gas Sensor>

Figure 1:
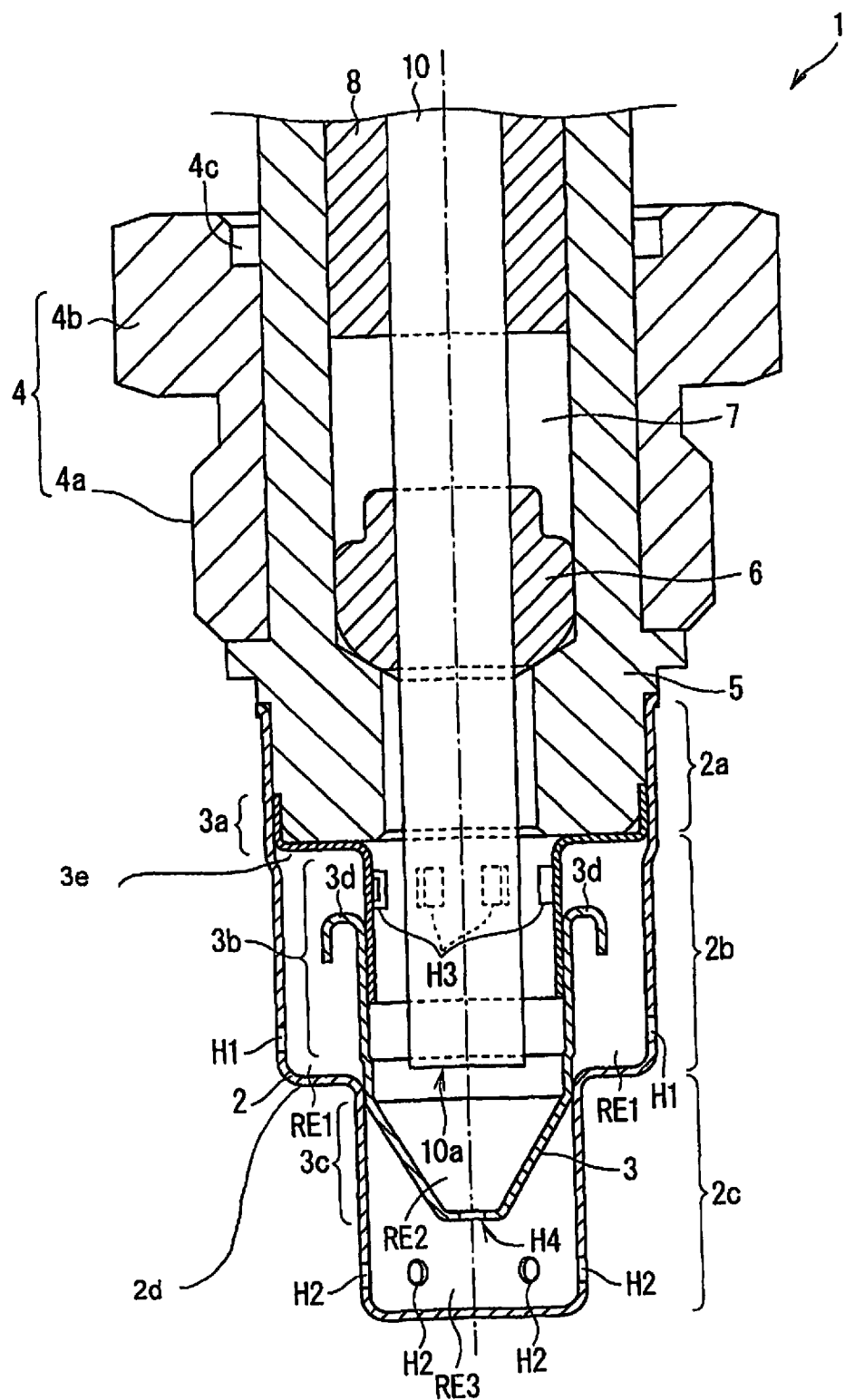
FIG. 1 is a cross-sectional view exemplarily illustrating an internal configuration of a main part of a gas sensor 1 as a responsivity inspection target.

FIG. 1 is a cross-sectional view exemplarily illustrating an internal configuration of a main part of a gas sensor 1 (more specifically, a body part thereof) as a target of responsivity inspection performed in the present preferred embodiment. In the present preferred embodiment, the gas sensor 1 is configured to detect a predetermined gas component (for example, NOx) through a sensor element 10 provided inside thereof. The sensor element 10 is an elongated prismatic or thin plate member mainly made of oxygen ion conducting solid electrolyte ceramics such as zirconia. The configuration of the sensor element will be described later.

The gas sensor 1 mainly includes, in addition to the sensor element 10, an outer protection cover 2, an inner protection cover 3, a fixing bolt 4, and a housing 5.

The outer protection cover 2 and the inner protection cover 3 are substantially cylindrical exterior members protecting part of the sensor element 10, which directly contacts a measurement gas when used, specifically, a distal end part 10a provided with, for example, a gas inlet 104, a first inner space 102, and a second inner space 103 to be described later. The outer protection cover 2 and the inner protection cover 3 form a double-layered structure as illustrated in FIG. 1, and are coaxially disposed. The distal end part 10a of the sensor element 10 is disposed in a space surrounded by the inner protection cover 3.

The outer protection cover 2 roughly includes a cylindrical fitting part 2a including an open end and fitted with the housing 5 at the open end, a cylindrical middle part 2b provided continuously with the fitting part 2a and having a diameter substantially identical to that of the fitting part 2a, and a leading end part 2c as a bottomed tube having a sectional diameter smaller than that of the middle part 2b. The fitting part 2a, the middle part 2b, and the leading end part 2c are coaxially disposed. The middle part 2b and the leading end part 2c are provided continuously with each other through a bending surface 2d orthogonal to an extending direction of the entire outer protection cover 2.

A plurality of first through-holes H1 are provided to the middle part 2b at positions closer to the leading end part 2c. The first through-holes H1 are provided at equal intervals in a circumferential direction of the middle part 2b. A plurality of second through-holes H2 are provided on a side surface of the leading end part 2c at positions closer to a bottom part of the side surface. The second through-holes H2 are provided at equal intervals in a circumferential direction of the leading end part 2c.

The inner protection cover 3 roughly includes a cylindrical fitting part 3a including an open end and fitted with the housing 5 at the open end, a cylindrical middle part 3b provided continuously with the fitting part 2a and having a diameter smaller than that of the fitting part 2a, and a truncated conical leading end part 3c provided continuously with the middle part 3b. A protruding part 3d is provided to the middle part 3b across a circumferential direction of the middle part 3b so as to protrude outwardly with sectionally U-shaped. The fitting part 3a, the middle part 3b, and the leading end part 3c are coaxially disposed. The fitting part 3a and the middle part 3b are provided continuously with each other through a bending surface 3e orthogonal to the extending direction of the entire outer protection cover 2.

Further, a plurality of third through-holes H3 are provided to the middle part 3b at positions closer to the bending surface 3e. The third through-holes H3 are provided at equal intervals in the circumferential direction of the middle part 3b. In addition, a fourth through-hole H4 is provided at a center of a bottom part of the leading end part 3c.

The positions of the first through-holes H1, the second through-holes H2, the third through-holes H3, and the fourth through-hole H4 illustrated in FIG. 1 and the numbers thereof are merely exemplary and not intended to limit the present invention.

Since the outer protection cover 2 and the inner protection cover 3 have the configuration described above, when the gas sensor 1 is used or inspected by an inspection apparatus 1000 to be described later, an external atmosphere of the gas sensor 1 first flows from the outside into a region RE1 between the middle part 2b of the outer protection cover 2 and the middle part 3b of the inner protection cover 3 through the first through-holes H1. Then, while being subjected to a straightening effect by the protruding part 3d, the atmosphere having flowed into the region RE1 enters, through the third through-holes H3, a region RE2 inside the inner protection cover 3 in which the distal end part 10a of the sensor element 10 is disposed. Part of the atmosphere having entered the region RE2 is taken into the sensor element 10 and used to calculate the concentration of a measurement gas. The atmosphere not having taken into the sensor element 10 flows out from the region RE2 to a region RE3 between the leading end part 3c of the inner protection cover 3 and the leading end part 2c of the outer protection cover 2 through the fourth through-hole H4. The external atmosphere of the gas sensor 1 is allowed to flow in and out through the second through-holes H2 at the leading end part 2c of the outer protection cover 2, and thus, the atmosphere having flowed out from the region RE2 to the region RE3 flows out through the second through-holes H2 together with the atmosphere taken from outside of the gas sensor 1 into the region RE3 through the second through-holes H2.

The fixing bolt 4 is a ring member used to fix a sensor body part 1 to a measurement position. The fixing bolt 4 includes a bolt part 4a with screw thread, and a holding part 4b held when the bolt part 4a is screwed. The bolt part 4a is screwed with a nut provided at an attachment position for the sensor body part 1. For example, when the bolt part 4a is screwed with a nut part provided to an exhaust pipe of an automobile, the sensor body part 1 is fixed to the exhaust pipe in a manner that a portion of the sensor body part 1 closer to the outer protection cover 2 is exposed in the exhaust pipe. In the present preferred embodiment, the bolt part 4a is also used to attach the gas sensor 1 to the inspection apparatus 1000 to be described later.

As illustrated in FIG. 1, inside the gas sensor 1, the sensor element 10 is fitted at axial center positions of a plurality of insulators and a plurality of sealing members (talc) adjacently disposed in an alternate manner, except for the distal end part 10a provided with the gas inlet and the like. Although FIG. 1 illustrates two insulators 6 and 8 and one sealing member 7 provided therebetween, practically, another sealing member and another insulator are additionally fitted in this order adjacent to the insulator 8. In addition, the two insulators 6 and 8 and the sealing member 7 therebetween are fitted with an inner cylindrical part of the substantially cylindrical housing 5. The housing 5 has one end fitted with the outer protection cover 2 and the inner protection cover 3, and the other end fitted with another cover (not illustrated) inserted in a recess 4c, and the fixing bolt 4 is secured to an outer periphery of the housing 5.

With the configuration described above, an atmosphere around the distal end part 10a of the sensor element 10 (an atmosphere inside the outer protection cover 2 and the inner protection cover 3) is completely separated from an external atmosphere when the gas sensor 1 is attached to a predetermined position, which allows accurate measurement of the concentration of a target gas component in the measurement gas.

<Exemplary Configuration of Sensor Element>

Figure 2:
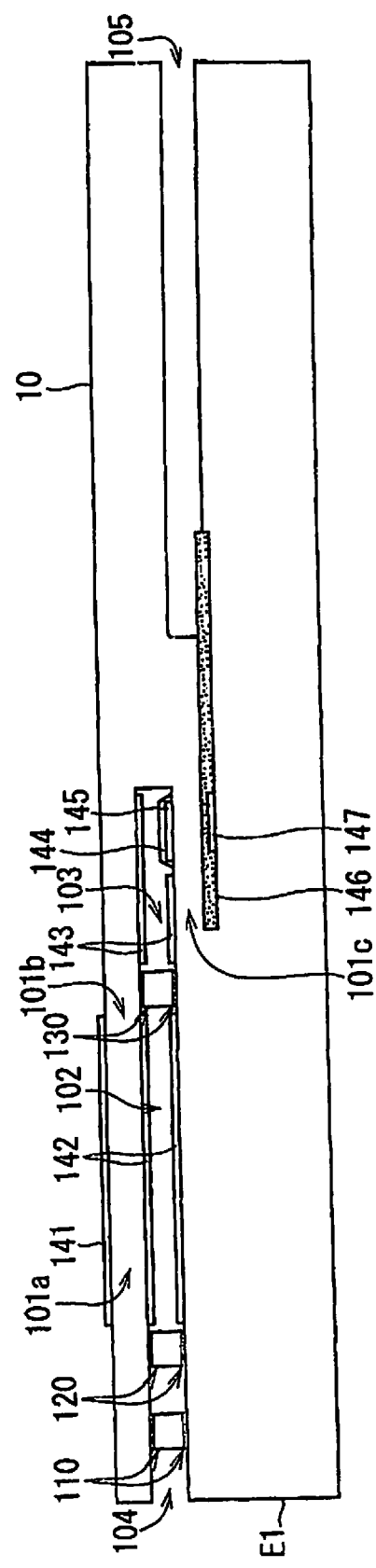
FIG. 2 is a cross-sectional view schematically illustrating an exemplary configuration of a sensor element 10 provided to the gas sensor 1.

FIG. 2 is a cross-sectional view schematically illustrating an exemplary configuration of the sensor element 10 provided to the gas sensor 1. FIG. 2 illustrates a configuration of the sensor element 10 when the sensor element 10 is a limiting current type NOx sensor element made of ceramics containing zirconia as a primary component, which is an oxygen ion conducting solid electrolyte.

The sensor element 10 is what is called a serial double-chamber structure sensor element having a configuration in which the first inner space 102 is communicated with the gas inlet 104 open to an outer space through a first diffusion control part 110 and a second diffusion control part 120, and the second inner space 103 is communicated with the first inner space 102 through a third diffusion control part 130. In the gas sensor 1, the sensor element 10 is disposed so that an end part E1 thereof at which the gas inlet 104 is provided coincides with the distal end part 10a in FIG. 1. The concentration of NOx in the measurement gas is calculated by executing a process described below using the sensor element 10.

First, the oxygen concentration of the measurement gas introduced into the first inner space 102 is adjusted substantially constant through a pumping operation (pumping in or pumping out of oxygen) of a main pump cell which is an electrochemical pump cell including an external pump electrode 141 provided to an outer surface of the sensor element 10, an internal pump electrode 142 provided in the first inner space 102, and a ceramic layer 101a between these electrodes, and then the gas is introduced into the second inner space 103. In the second inner space 103, oxygen in the measurement gas is pumped out through a pumping operation of an auxiliary pump cell which is also an electrochemical pump cell including the external pump electrode 141, an auxiliary pump electrode 143 provided in the second inner space 103, and a ceramic layer 101b between these electrodes, thereby the measurement gas is brought into an adequate low-oxygen partial pressure state.

NOx of the measurement gas in the low-oxygen partial pressure state is reduced or degraded at a measurement electrode 145 covered with a protection layer 144 and provided in the second inner space 103. Then, oxygen ions generated through the reduction or degradation are pumped out by a measurement pump cell which is an electrochemical pump cell including the measurement electrode 145, a reference electrode 147 provided in a porous alumina layer 146 communicated with a reference gas inlet 105, and a ceramic layer 101c between these electrodes. Then, the NOx concentration of the measurement gas is calculated based on a linear relation between the current value of current (NOx current) generated at the pumping and the NOx concentration.

The pumping by the main pump cell, the auxiliary pump cell, and the measurement pump cell is achieved through a variable power source (not illustrated) that applies, between the pump electrodes included in each pump cell, voltage in accordance with respective oxygen concentration in the first inner space 102, in the second inner space 103, and near the measurement electrode 145.

The sensor element 10 is provided with a heater part (not illustrated), and the above-described operation is performed while the sensor element 10 is heated at a temperature of about 600° C. to 700° C. through energization to the heater part. Accordingly, inspection at the inspection apparatus to be described later is performed after the sensor element is heated to the above temperature.

<Outline of Responsivity Inspection>

The following describes the outline of responsivity inspection of the gas sensor 1 performed in the present preferred embodiment.

As described above, in the gas sensor 1, the distal end part 10a including the gas inlet 104 of the sensor element 10, into which the measurement gas is introduced, is surrounded by the outer protection cover 2 and the inner protection cover 3, and thus a certain time is taken until the measurement gas having flowed into the outer protection cover 2 reaches the measurement electrode 145 and causes an output change in accordance with the concentration of a component to be measured. Real-time measurement of the concentration of a gas component to be measured in the measurement gas requires that the gas sensor 1 changes its output, following, as fast as possible, a concentration change actually occurring in the measurement gas. This followability of the output change in response to the concentration change of the measurement gas is referred to as responsivity.

In the present preferred embodiment, the responsivity is inspected based on the degree of change of the sensor output when the measurement gas having a known concentration of target component gas is caused to flow in a pulse manner.

Figure 3:
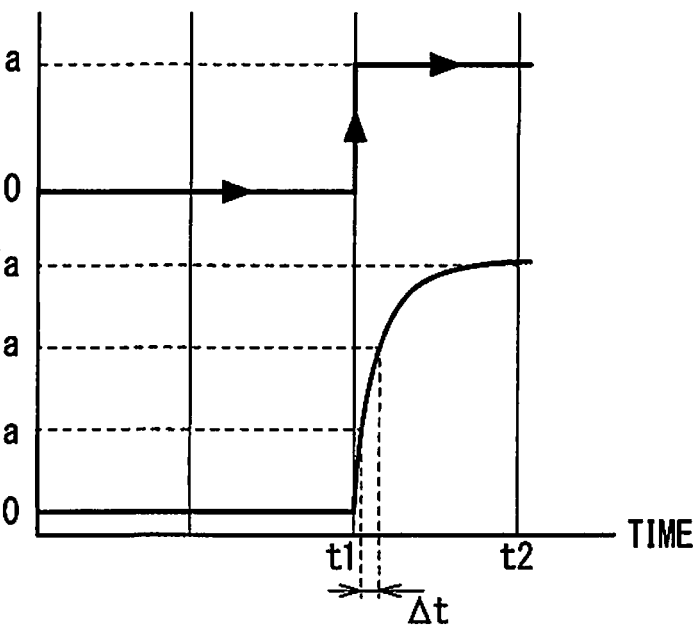
FIG. 3 is a diagram for description of responsivity inspection of the gas sensor 1.

FIG. 3 is a diagram for description of the responsivity inspection of the gas sensor 1 performed in the present preferred embodiment. More specifically, FIG. 3 shows a flow rate profile ((a) of FIG. 3) of the gas for inspection at the responsivity inspection of the gas sensor 1, and a sensor output current profile ((b) of FIG. 3) indicating change of sensor output current occurring in the gas sensor 1 when provided with the gas for inspection having the flow rate profile.

In the present preferred embodiment, in a case that supply of a gas for inspection at constant flow rate a is started at time t1 to a predetermined closed space (chamber) in which the gas sensor 1 is present as illustrated in (a) of FIG. 3, and then an output (sensor output current) from the gas sensor 1 becomes constant value 1a equivalent to the concentration of the detection target gas component at time t2 as illustrated in (b) of FIG. 3, time Δt taken when a sensor output signal increases from a value of 0.33 Ia to a value of 0.66 Ia is determined to be a responsivity evaluation value. The gas for inspection contains a detection target gas component for the gas sensor 1 and has a constant component ratio. Then, it is determined based on the responsivity evaluation value whether the responsivity inspection is successful.

Specifically, the sensor output current used for evaluation in the responsivity inspection is, for example, current (referred to as Ip0) flowing between the external pump electrode 141 and the internal pump electrode 142 at the main pump cell.

<Schematic Configuration of Inspection Apparatus>

FIG. 4 is a diagram schematically illustrating a configuration of the inspection apparatus 1000 configured to perform the responsivity inspection. The inspection apparatus 1000 mainly includes a chamber 1001 in which the gas sensor 1 to be inspected is disposed and into which a gas for inspection flows, a gas supply source 1002 configured to generate the gas for inspection, a gas exhaust part 1003 through which the gas for inspection having passed through the chamber 1001 is exhausted, and a responsivity inspection processing part 1004 including a CPU, a ROM, and a RAM and configured to control processing for the responsivity inspection performed at the inspection apparatus 1000.

The chamber 1001 is disposed extending in one direction in a horizontal plane. The chamber 1001 is provided with four inspection positions A to D sequentially from an upstream side on the right side in FIG. 4, and the gas sensor 1 to be inspected is set at each of the inspection positions A to D. This configuration allows the inspection to be performed simultaneously in parallel at inspection positions A to D in the inspection apparatus 1000. The chamber 1001 is supplied with a gas for inspection generated at the gas supply source 1002 as illustrated with arrow AR1. The gas for inspection having passed through the chamber 1001 is ejected to the gas exhaust part 1003 as illustrated with arrow AR2, and exhausted through the gas exhaust part 1003 as appropriate.

When the responsivity inspection is performed in the inspection apparatus 1000 having the above-described configuration, the gas sensor 1 as a responsivity inspection target is set at each of the four inspection positions A to D. Although FIG. 4 schematically illustrates the gas sensor 1, more specifically, the gas sensor 1 is set at each of the four inspection positions A to D so that a part of the gas sensor 1, that is below the bolt part 4a illustrated in FIG. 1, is positioned in the chamber 1001.

In response to an instruction to execute the inspection from the responsivity inspection processing part 1004, the gas for inspection is supplied at a constant flow rate from the gas supply source 1002 to achieve such a gas flow rate profile as exemplarily illustrated in (a) of FIG. 3. The flow rate may be set as appropriate as long as the gas for inspection well arrives inside the outer protection cover 2 of the gas sensor 1 set at each of the inspection positions A to D. For example, the flow rate may be determined to be a value close to a gas flow rate under an environment in which the gas sensor 1 is disposed when actually used, or may be determined in terms of efficiency of the inspection.

At the start of supply of the gas for inspection, the responsivity inspection processing part 1004 starts monitoring the sensor output current of each of the four gas sensors 1 to be inspected, thereby to obtain such an output profile as exemplarily illustrated in (b) of FIG. 3. The responsivity evaluation value corresponding to Δt in (b) of FIG. 3 is calculated from each profile. Then, if the responsivity evaluation value is not larger than a predetermined threshold, it is determined that the gas sensor 1 has favorable responsivity, and the determination result is provided to processing at a later stage.

The gas for inspection having passed through the chamber 1001 is ejected to the gas exhaust part 1003 as illustrated with arrow AR2 in FIG. 4.

When the responsivity inspection is performed in this manner, it is required that equivalent inspection results are obtained at all of the inspection positions A to D. The following exemplarily describes two specific configurations of the chamber 1001, which satisfy this requirement.

(First Exemplary Configuration of Chamber)

Figure 5:
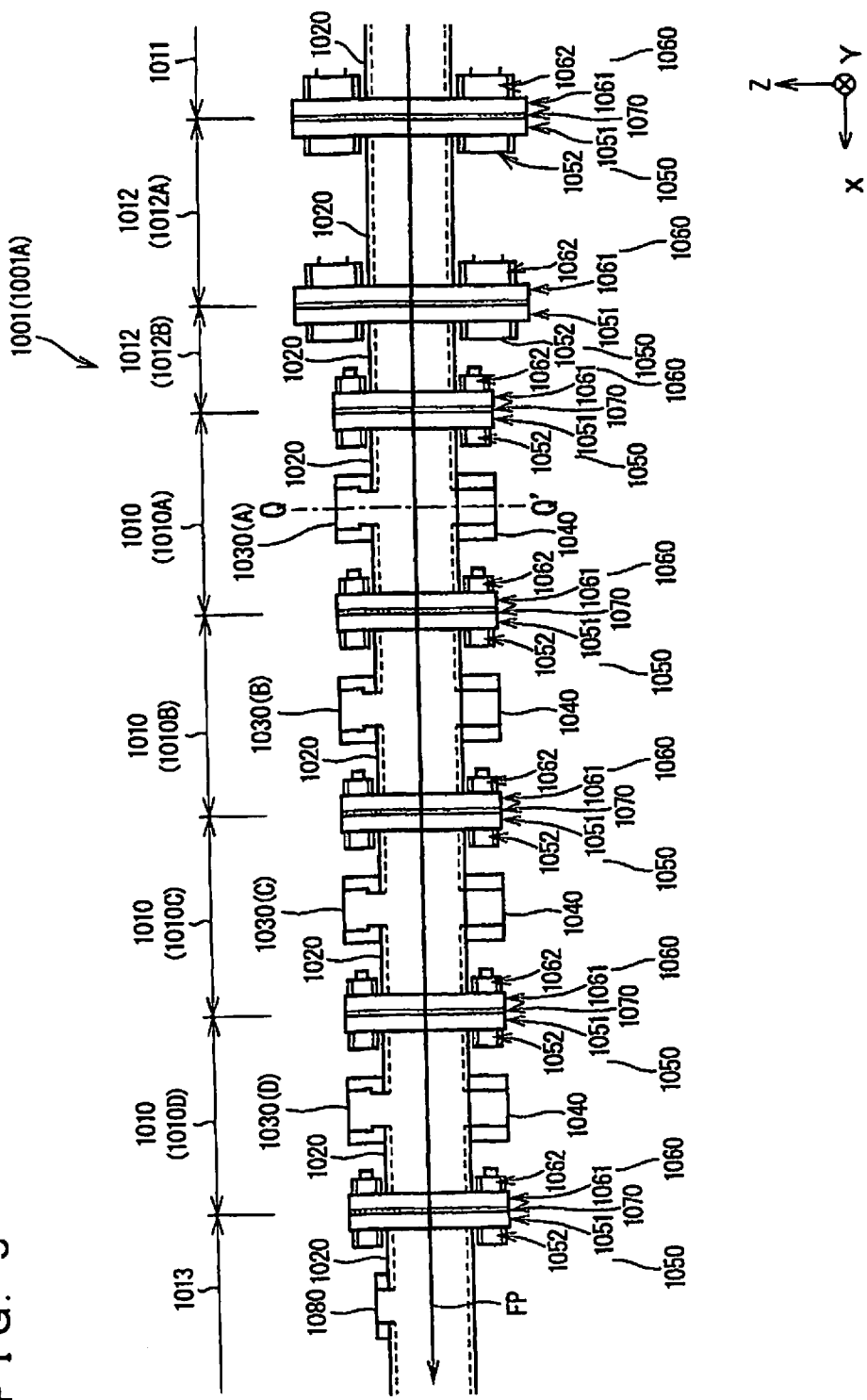
FIG. 5 is a vertical cross-sectional view along a longitudinal direction of a chamber 1001A having a first exemplary configuration.
Figure 6:
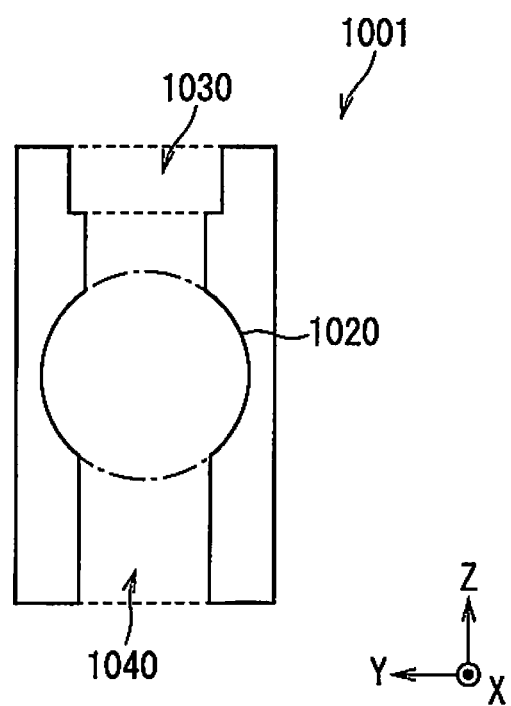
FIG. 6 is a cross-sectional view orthogonal to the longitudinal direction of the chamber 1001A, taken along line Q-Q' illustrated in FIG. 5.

FIG. 5 is a vertical cross-sectional view along a longitudinal direction of the chamber 1001 (1001A) having a first exemplary configuration. FIG. 6 is a cross-sectional view vertical to the longitudinal direction of the chamber 1001A taken along line Q-Q' illustrated in FIG. 5. FIG. 5 and the following drawings are shown in a right-handed xyz coordinate system in which the positive x-axis direction is a direction that is the longitudinal direction of the chamber 1001A and in which a gas for inspection flows through the chamber 1001A, and the positive z-axis direction is a vertically upward direction.

The chamber 1001A mainly includes four inspection pipe units 1010 (1010A to 1010D), an upstream pipe unit 1011, an auxiliary pipe unit 1012, and a downstream pipe unit 1013. The inspection pipe units 1010, the upstream pipe unit 1011, the auxiliary pipe unit 1012, and the downstream pipe unit 1013 each include a cylindrical gas flowing part 1020 having an identical diameter.

In the chamber 1001A, the upstream pipe unit 1011, the auxiliary pipe unit 1012, the four inspection pipe units 1010, and the downstream pipe unit 1013 are joined with each other in this order from the upstream side (side closer to the gas supply source) so that the respective gas flowing parts 1020 are coaxially disposed. With this configuration, one gas flow path FP extending in one direction (x axial direction) in a horizontal plane is formed in the chamber 1001A. The four inspection pipe units 1010A to 1010D are joined with each other in this order from the upstream side.

Each of the inspection pipe units 1010 includes, in addition to the gas flowing part 1020, an inspected sensor disposing part 1030 as a hole provided vertically to the gas flowing part 1020, and a temperature sensor disposing part 1040 as a hole provided vertically to the gas flowing part 1020 at a position facing the inspected sensor disposing part 1030. More specifically, the inspected sensor disposing part 1030 and the temperature sensor disposing part 1040 are provided so that the former extends vertically upward and the latter extends vertically downward when the gas flowing part 1020 is disposed along a horizontal plane. Since the four inspection pipe units 1010A to 1010D have an identical structure, the inspected sensor disposing parts 1030 provided to the respective units are positioned at equal intervals in the extending direction of the gas flow path FP, and thus the inspection positions A to D are provided at equal intervals.

The inspected sensor disposing parts 1030 provided to the four inspection pipe units 1010A to 1010D respectively correspond to the inspection positions A to D at which the gas sensors 1 to be inspected are disposed. The sensor element 10 is inserted into the inspected sensor disposing part 1030 so that a side of the sensor element 10, which is closer to the outer protection cover 2, protrudes into the gas flowing part 1020, and is fixed to the inspected sensor disposing part 1030 by the bolt part 4a. The degree of the protrusion of the outer protection cover 2 into the gas flowing part 1020 may be determined as appropriate in accordance with, for example, the shapes of the outer protection cover 2 and the inner protection cover 3, and the positions and sizes of the first to fourth through-holes H1 to H4 provided to the outer protection cover 2 and the inner protection cover 3.

A temperature sensor is inserted into the temperature sensor disposing part 1040 to monitor the temperature of the gas for inspection near the inspected sensor disposing part 1030. The configuration of the temperature sensor is not particularly limited. The temperature sensor inserted into the gas flowing part 1020 at the temperature sensor disposing part 1040 also functions as a kind of straightening member for the gas for inspection flowing through the gas flow path FP.

However, the temperature sensor does not necessarily need to be provided to each of the inspection pipe units 1010, and the temperature sensor disposing part 1040 may be omitted. Alternatively, a member that provides only a straightening effect may be inserted into a hole provided similarly to the temperature sensor disposing part 1040.

The upstream pipe unit 1011 is a pipe unit connected with the gas supply source 1002. FIG. 4 illustrates only one gas supply source 1002 for simplicity of description. When a plurality of gasses are mixed to generate the gas for inspection, however, the inspection apparatus 1000 may include different gas supply sources 1002 for a plurality of kinds of gasses, and the plurality of kinds of gasses supplied from the gas supply sources 1002 through different branch pipes (not illustrated) joined to the upstream pipe unit 1011 may be mixed at a predetermined ratio in the upstream pipe unit 1011, heated to a predetermined temperature, and then provided to the chamber 1001.

The auxiliary pipe unit 1012 connects the upstream pipe unit 1011 to the inspection pipe unit 1010A, which is positioned on a most upstream side among the four inspection pipe units 1010. In the configuration illustrated in FIG. 5, two auxiliary pipe units 1012A and 1012B are disposed in this order from the upstream side.

The downstream pipe unit 1013 is a pipe unit that is connected with the gas exhaust part 1003 and through which the gas for inspection having passed through the inspection pipe units 1010 is exhausted. The downstream pipe unit 1013 is connected with the inspection pipe unit 1010D positioned on a most downstream side among the four inspection pipe units 1010. The downstream pipe unit 1013 is provided with a concentration sensor disposing part 1080 in which a concentration sensor is disposed, the concentration sensor being configured to monitor the concentration of a target gas component for the gas sensor 1 in the gas for inspection having passed through the gas flow path FP.

The upstream pipe unit 1011, the two auxiliary pipe units 1012, the four inspection pipe units 1010, and the downstream pipe unit 1013 each include a first coupling part 1050 and a second coupling part 1060 for achieving coupling with adjacent pipe units. More specifically, each pipe unit is provided with the first coupling part 1050 at an end part thereof on the upstream side, and provided with the second coupling part 1060 at an end part thereof on the downstream side. The first coupling part 1050 and the second coupling part 1060 include flat plate-shaped contact portions 1051 and 1061, respectively, provided vertically to the gas flowing part 1020 on an outer periphery of the gas flowing part 1020. Through-holes are provided at four positions on the contact portions 1051 and 1061 around the gas flowing part 1020. Bolts 1052 inserted into the through-holes of the contact portion 1051 provided to one of two adjacent pipe units penetrate through the respective through-holes of the contact portion 1061 provided to the other pipe unit, and parts of the bolts 1052 protruding out of the through-holes are screwed with nuts 1062, thereby coupling the two adjacent pipe units.

However, at coupling of the first coupling part 1050 and the second coupling part 1060, straightening plates 1070 are interposed between the adjacent inspection pipe units 1010, between the upstream pipe unit 1011 and the auxiliary pipe unit 1012A, and between the inspection pipe unit 1010D and the downstream pipe unit 1013. FIG. 7 is a front view of each of the straightening plates 1070. The straightening plate 1070 is a thin plate member including, at a central part, a rectangular opening 1070a having a width (size in the y-axis direction) w and a height (size in the z-axis direction) h. The straightening plate 1070 is interposed orthogonally to the gas flow path FP so that the opening 1070a and the gas flow path FP formed by the gas flowing part 1020 are coaxially disposed as illustrated in FIG. 7.

More specifically, the width w of the opening 1070a is set to be same as the diameter of the flow path FP (gas flowing part 1020), and the height h of the opening 1070a is set to be smaller than the width w. When the gas flow path FP extends in one direction (x axial direction) in a horizontal plane, the opening 1070a is provided to have its longitudinal direction along a direction (y-axis direction) orthogonal to the one direction in the horizontal plane. The straightening plate 1070 is fixed between two adjacent pipe units in a manner that the bolts 1052 used to connect the two pipe units are also inserted into fixation through-holes 1070b provided at four positions around the opening 1070a.

With this configuration, the straightening plate 1070 including the rectangular opening 1070a whose longitudinal direction being along the horizontal direction is provided upstream of each of the four inspected sensor disposing parts 1030 at the inspection positions A to D.

Since the inspection pipe units 1010A to 1010D have an identical structure as described above, and the inspection positions A to D are provided at equal intervals in the extending direction of the gas flow path FP, the distance between each of the inspected sensor disposing parts 1030 (each of the inspection positions A to D) and the corresponding straightening plate 1070 provided upstream thereof is constant.

When the responsivity inspection is performed in the chamber 1001A having the configuration described above, a predetermined temperature sensor and a predetermined concentration sensor are respectively disposed at the temperature sensor disposing part 1040 and the concentration sensor disposing part 1080 in advance, and then, the gas sensors 1 as responsivity inspection targets are disposed at the inspected sensor disposing parts 1030 (inspection positions A to D) of the respective four inspection pipe units 1010A to 1010D. Then, the gas for inspection is supplied based on such a gas flow rate profile as exemplarily illustrated in (a) of FIG. 3, and the responsivity inspection is performed on the gas sensors 1 in parallel.

In this case, the chamber 1001A is configured to have no significant difference in the state of the flow (flow speed distribution) of the gas for inspection among positions of the gas sensors 1 disposed at the respective inspection positions A to D (more specifically, inside the outer protection cover 2 in which the sensor element 10 is provided). In other words, uniformity of the flow speed distribution is achieved among the inspection positions.

This effect is provided due to the fact that the configuration including the above-described straightening plate 1070 is employed, so that the gas for inspection straightened through the opening 1070a of the straightening plate 1070 is supplied near the gas sensors 1 disposed at the four inspection positions A to D.

In addition, no significant difference is produced in fluctuation of the responsivity evaluation value obtained through the responsivity inspection at each of the inspection positions. This effect is provided because the uniformity of the flow speed distribution is achieved among the inspection positions as described above. This means that the inspection apparatus 1000 including the chamber 1001A is superior in performing the same evaluation at any inspection place, which is required when the responsivity inspection is performed simultaneously in parallel at a plurality of inspection places provided to one gas flow path.

The gas for inspection near the opening 1070a preferably has a flow speed of 12 m/sec or more at the responsivity inspection. With this configuration, the above-described fluctuation of the responsivity evaluation value at the four inspection positions A to D is favorably reduced. Thus, the size of the opening 1070a and the flow rate of the gas for inspection at the responsivity inspection are preferably set to achieve the flow speed described above.

(Second Exemplary Configuration)

Figure 8:
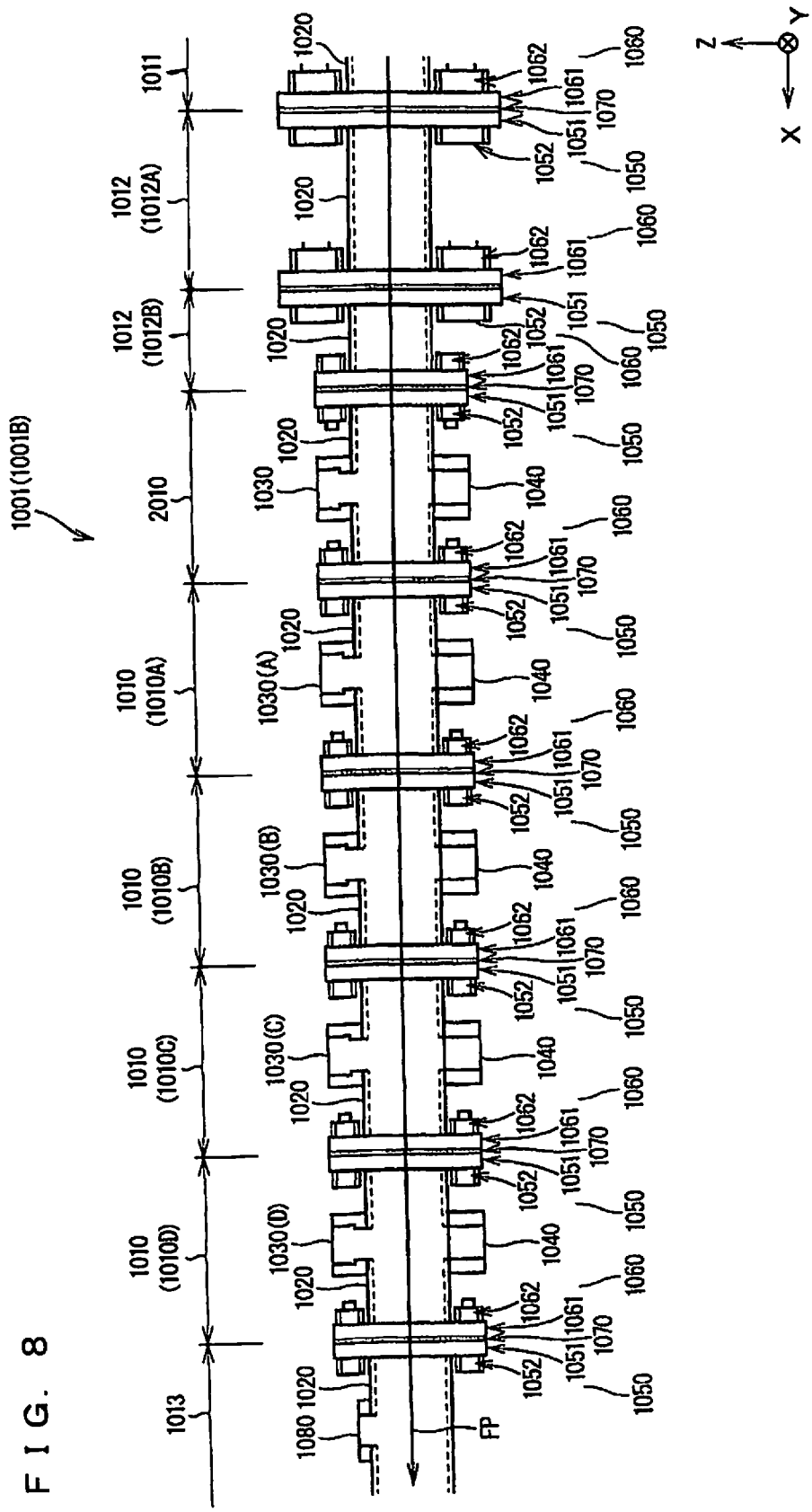
FIG. 8 is a vertical cross-sectional view along a longitudinal direction of a chamber 1001B having a second exemplary configuration.

FIG. 8 is a vertical cross-sectional view along a longitudinal direction of a chamber 1001B having a second exemplary configuration. The chamber 1001B illustrated in FIG. 8 is obtained by modifying the chamber 1001A having the first exemplary configuration.

Specifically, the chamber 1001B has a configuration in which a dummy pipe unit 2010 is inserted between the auxiliary pipe unit 1012B and the inspection pipe unit 1010A that provides the inspection position A in the chamber 1001A having the first exemplary configuration. The other configuration is same as that of the chamber 1001A, and thus detailed description thereof is omitted.

The dummy pipe unit 2010 has a configuration identical to that of each of the inspection pipe units 1010. Specifically, completely similarly to the inspection pipe unit 1010, the dummy pipe unit 2010 includes the gas flowing part 1020, the inspected sensor disposing part 1030, the temperature sensor disposing part 1040, the first coupling part 1050, and the second coupling part 1060. Connection with the auxiliary pipe unit 1012B adjacent on the upstream side, and connection with the inspection pipe unit 1010A adjacent on the downstream side are achieved similarly to connection between other pipe units. In addition, the straightening plates 1070 illustrated in FIG. 7 are interposed between the dummy pipe unit 2010 and the auxiliary pipe unit 1012B and between the dummy pipe unit 2010 and the inspection pipe unit 1010A.

Naturally, the interval between the inspected sensor disposing part 1030 of the dummy pipe unit 2010 and the inspected sensor disposing part 1030 of the adjacent inspection pipe unit 1010A in the extending direction of the gas flow path FP is same as the interval between the inspected sensor disposing parts 1030. In other words, all of the inspected sensor disposing parts 1030 including the inspected sensor disposing part 1030 of the dummy pipe unit 2010 are disposed at equal intervals in the chamber 1001B.

The distance between the dummy pipe unit 2010 and the straightening plate 1070 upstream thereof is same as the distance between each of the inspection pipe units 1010 and the straightening plate 1070 upstream thereof.

When the responsivity inspection is performed in the inspection apparatus 1000 including the chamber 1001B, a dummy sensor having a shape and a structure identical to those of the gas sensor 1 is disposed at the inspected sensor disposing part 1030 of the dummy pipe unit 2010, instead of disposing the gas sensor 1 to be inspected. In other words, the inspected sensor disposing part 1030 of the dummy pipe unit 2010 serves as a dummy sensor disposing part. Similarly to the temperature sensor disposing part 1040 of each of the inspection pipe units 1010, the temperature sensor disposing part 1040 of the dummy pipe unit 2010 is provided with a temperature sensor.

When the responsivity inspection is performed in the inspection apparatus 1000 including the chamber 1001B having the configuration, fluctuation of the responsivity evaluation values obtained from the gas sensors 1 disposed at the inspection positions A to D is further reduced as compared to the responsivity inspection in the inspection apparatus 1000 including the chamber 1001A. Preferably, the fluctuation of the responsivity evaluation value at each of the inspection positions A to D is substantially zero. Accordingly, the degree of the fluctuation of the responsivity evaluation value has no difference among the inspection positions.

This effect is achieved by treating the inspection pipe unit 1010A, which is disposed on at the most upstream position among the four inspection positions in the chamber 1001A and provides the most upstream sided inspection position A, as if the second upstream sided inspection pipe unit 1010 in terms of the structure of the chamber, as a result that a configuration similar to that of the inspection pipe units 1010 is employed with the dummy pipe unit 2010, and a dummy sensor and a temperature sensor provided thereto, on the upstream of the inspection pipe unit 1010A. More specifically, the effect is achieved due to the fact that the respective upstream sides of the four inspection pipe units 1010A to 1010D in the gas flowing part 1020 have an identical configuration in the chamber 1001B, while the configuration on the upstream side of the inspection pipe unit 1010A in the gas flowing parts 1020 is different from that of other inspection pipe units in the chamber 1001A.

As a result of such a configuration with the dummy pipe unit 2010, the inspection pipe unit 1010D, which provides the inspection position D, is as if the fifth inspection pipe unit 1010 from the upstream side in terms of the structure of the chamber, but the degree of fluctuation of the responsivity evaluation value of the gas sensor 1 disposed at the inspection position D is equivalent to those of the gas sensors 1 disposed at other inspection positions.

As described above, according to the present preferred embodiment, in an inspection apparatus provided with a plurality of inspection positions halfway through one gas flow path to perform responsivity inspection on a plurality of gas sensors, a straightening plate provided with a rectangular opening having a longitudinal direction along the horizontal direction is provided upstream of each of the inspection positions, so that fluctuation of the responsivity evaluation value among the inspection positions can be reduced.

In addition, in the case a dummy pipe unit having a configuration identical to that of the inspection pipe unit is provided on further upstream side of the inspection pipe unit that provides an inspection position on the most upstream side, the fluctuation of the responsivity evaluation value among the inspection positions can be further reduced.

Modifications

In the above-described preferred embodiment, the four inspection positions are provided in the inspection apparatus 1000, but the number of inspection positions is not limited thereto, and the responsivity inspection with reduced fluctuation of the accuracy of the responsivity evaluation value can be performed with up to 10 inspection positions. When more than 10 inspection positions are provided, however, reduction of the temperature of a gas for inspection becomes significant, resulting in difference in inspection conditions among the inspection positions, which is not preferable.

The shapes of the outer protection cover and the inner protection cover of the gas sensor to be inspected are not limited to those exemplarily illustrated in the above-described preferred embodiment.

EXAMPLES

Responsivity Evaluation

As Example 1, the responsivity inspection was performed on the four gas sensors 1 by using the inspection apparatus 1000 including the chamber 1001A having the first exemplary configuration described above, and the fluctuation of the responsivity evaluation value at each of the inspection positions was evaluated.

The gas sensor 1 was a NOx sensor, a detection target gas component of which is NOx. The gas sensor 1 was checked to be a non-defective product in advance. The gas for inspection was prepared as following: first, air having a flow rate of 90 L/min and an LNG gas having a flow rate of 10 L/min were mixed and then heated to 350° C., so as to obtain a mixed gas having a flow rate of 100 L/min; subsequently, air having a flow rate of 26 L/min at room temperature was further mixed.

The inner diameter of the gas flowing part 1020 and the width w of the opening 1070a were 28 mm, and the height h of the opening 1070a was 10 mm. The length of the gas flowing part 1020 in each of the inspection pipe units 1010 was 90 mm.

Three straightening plates 1071, 1072, and 1073 having an opening different in shape from that of the straightening plate 1070 provided to the chamber 1001A were prepared as Comparative Examples 1 to 3. The straightening plate 1070 of the inspection apparatus 1000 according to Example 1 was replaced with each of the straightening plates 1071, 1072, and 1073 (except for the straightening plate 1070 between the upstream pipe unit 1011 and the auxiliary pipe unit 1012), and then the fluctuation of the responsivity evaluation value was evaluated. Any condition other than the straightening plate was same as that of Example 1.

FIGS. 9A to 11 are diagrams of the straightening plates 1071, 1072, and 1073, respectively, according to Comparative Examples 1 to 3.

Figure 9A:
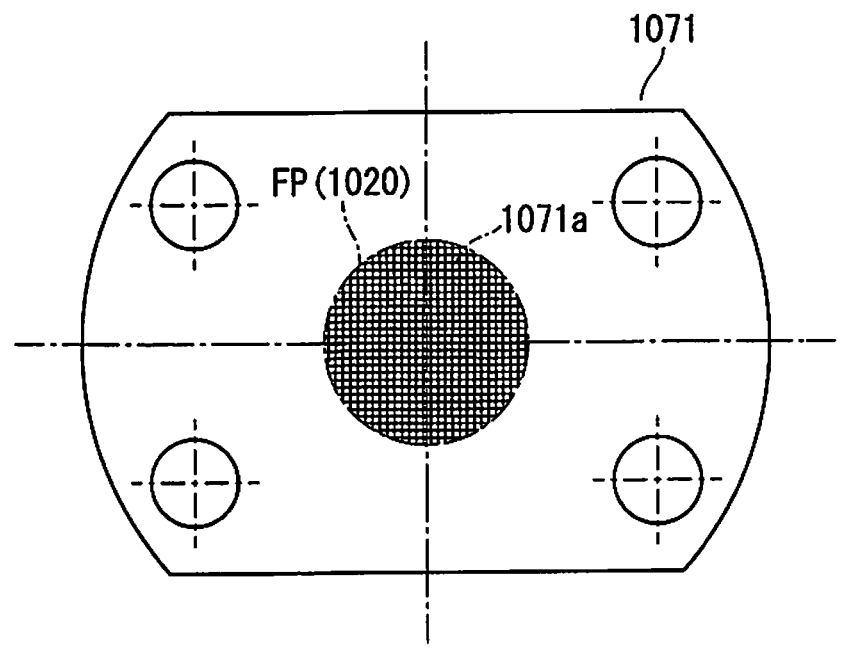
FIGS. 9A and 9B are diagrams illustrating a straightening plate 1071 according to Comparative Example 1.
Figure 9B:
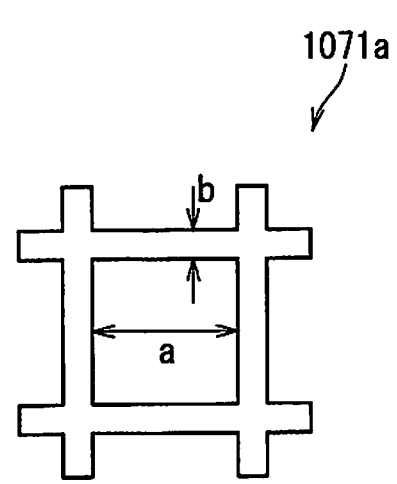

As illustrated in FIG. 9A, the straightening plate 1071 according to Comparative Example 1 includes a mesh opening 1071a at a central part thereof. The opening 1071a is provided at a position to come to cover the entire gas flow path FP (gas flowing part 1020) when the straightening plate 1071 is interposed between the first coupling unit 1050 and the second coupling unit 1060. As illustrated in FIG. 9B, each mesh of the opening has a square shape. In Comparative Example 1, the mesh has a side length a of 10 mm, and a thickness b of 2 mm.

Figure 10:
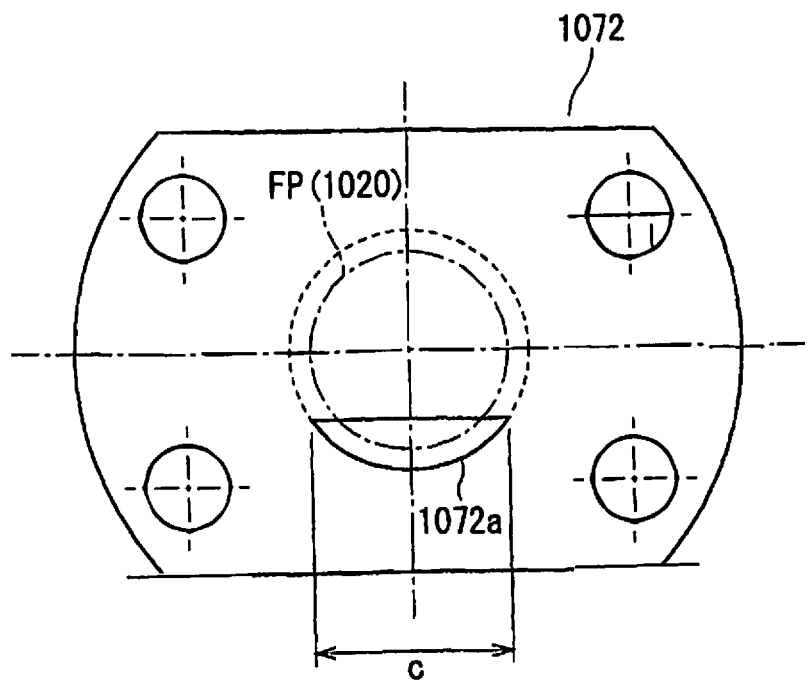
FIG. 10 is a diagram illustrating a straightening plate 1072 according to Comparative Example 2.

As illustrated in FIG. 10, the straightening plate 1072 according to Comparative Example 2 includes an arched opening 1072a. The opening 1072a comes to be positioned at a lower part of the gas flow path FP (gas flowing part 1020) in the vertical direction when the straightening plate 1072 is interposed between the first coupling unit 1050 and the second coupling unit 1060. Comparative Example 2 is a case in which only part of the opening 1072a is actually open to the gas flow path FP (the gas flowing part 1020) because a distance c between both ends of the opening 1072a in the horizontal direction is larger than the diameter of the gas flow path FP (the gas flowing part 1020).

Figure 11:
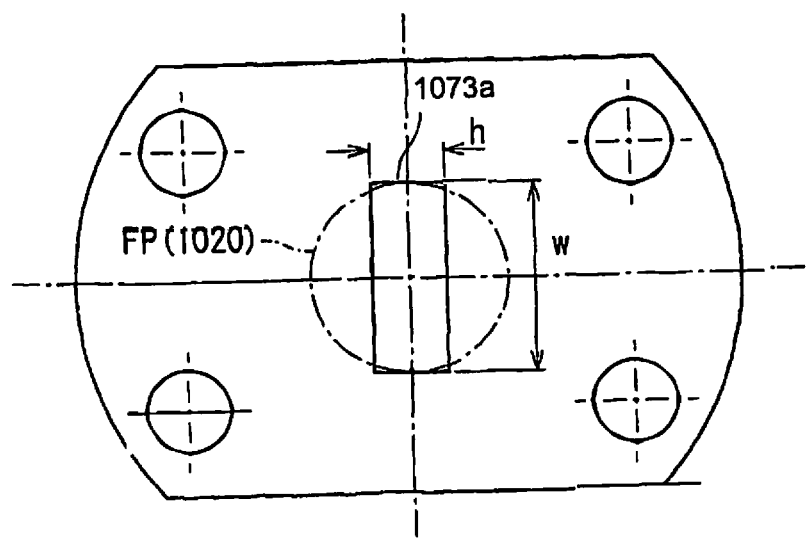
FIG. 11 is a diagram illustrating a straightening plate 1073 according to Comparative Example 3.

As illustrated in FIG. 11, the straightening plate 1073 according to Comparative Example 3 includes a rectangular opening 1073a at a central part thereof. When the gas flow path FP extends in one direction in a horizontal plane, the opening 1073a is provided to extend in the vertical direction in a vertical plane orthogonal to the one direction. In other words, the extending direction of the opening 1073a when the straightening plate 1073 according to Comparative Example 3 is interposed between the first coupling part 1050 and the second coupling part 1060 is orthogonal to the extending direction of the opening 1070a in the straightening plate 1070 provided to the chamber 1001A having the first exemplary configuration described above.

In addition, as Example 2, the responsivity inspection was performed on the four gas sensors 1 by using the inspection apparatus 1000 including the chamber 1001B having the second exemplary configuration described above, and the fluctuation of the responsivity evaluation value at each of the inspection positions was evaluated. Example 2 has a configuration same as that of Example 1, except for the dummy pipe unit 2010 having a configuration same as that of each of the inspection pipe units 1010.

The responsivity evaluation value was calculated three times at each of the inspection positions for each of the examples and the comparative examples.

FIGS. 12, 13, 14, 15, and 16 are diagrams of the responsivity evaluation values of the gas sensors 1 disposed at the inspection positions A to D (simply referred to as positions A to D in FIGS. 12 to 16), which were obtained by the inspection apparatus according to Example 1, Comparative Example 1, Comparative Example 2, Comparative Example 3, and Example 2, respectively. FIGS. 12 to 16 each show the maximum value, the minimum value, and the average value of the responsivity evaluation value obtained at each of the inspection positions A to D.

Figure 12:
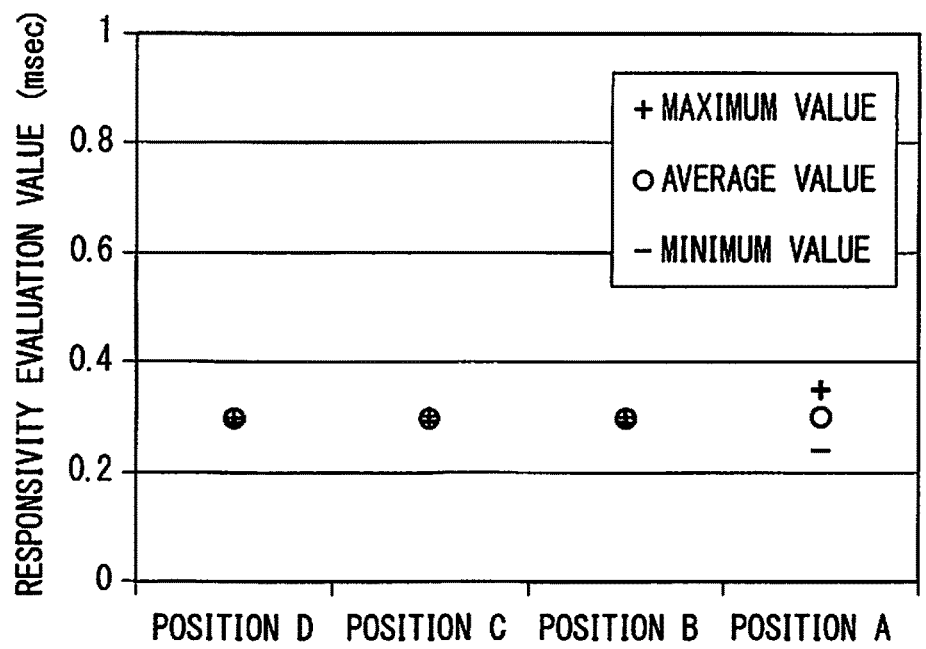
FIG. 12 is a diagram showing responsivity evaluation values of the gas sensor 1 disposed at inspection positions A to D, which are obtained by an inspection apparatus according to Example 1.

In comparison of FIGS. 12 to 15, the average value of the responsivity evaluation value is substantially constant at about 0.3 msec irrespective of the inspection positions in FIG. 12 showing a result of Example 1, and the fluctuation (difference between the maximum value and the minimum value) was about 0.1 msec at the inspection position A, but was substantially zero at the inspection positions B to D.

Figure 13:
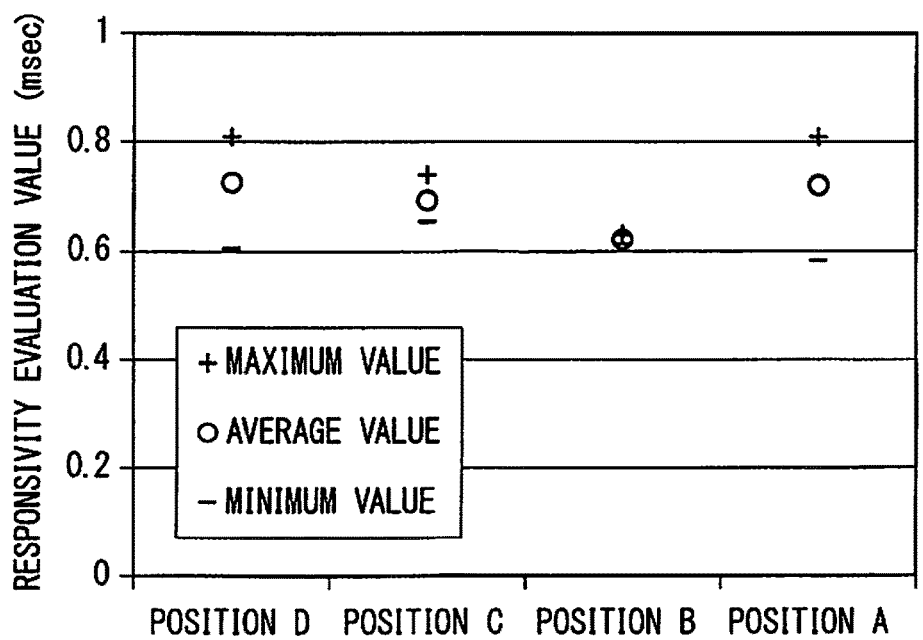
FIG. 13 is a diagram showing responsivity evaluation values of the gas sensor 1 disposed at inspection positions A to D, which are obtained by an inspection apparatus according to Comparative Example 1.
Figure 14:
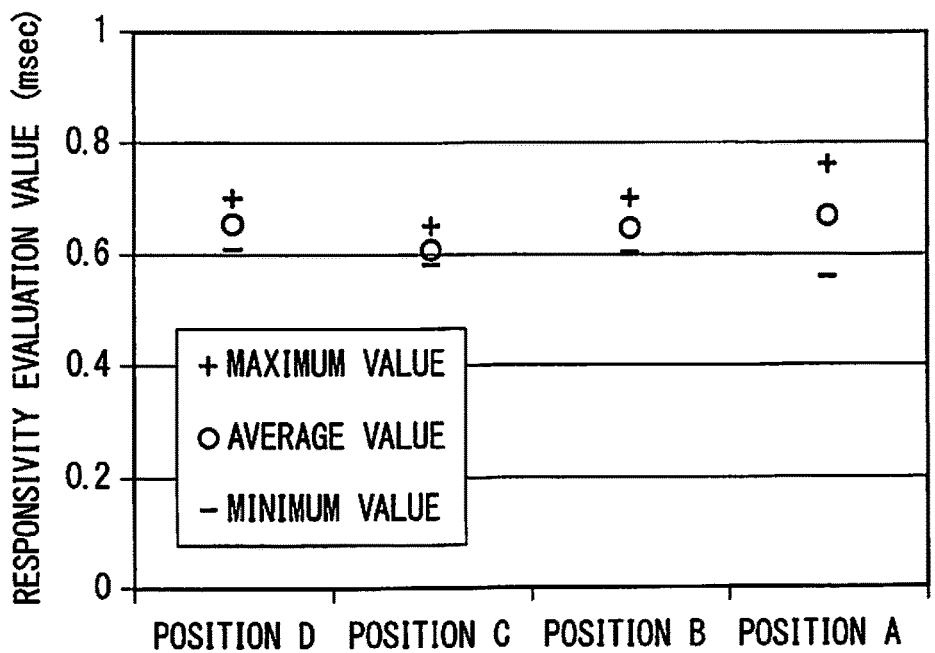
FIG. 14 is a diagram showing responsivity evaluation values of the gas sensor 1 disposed at inspection positions A to D, which are obtained by an inspection apparatus according to Comparative Example 2.

In FIGS. 13 and 14 showing results of Comparative Examples 1 and 2, the average value of the responsivity evaluation value and the fluctuation thereof differ among the inspection positions.

Figure 15:
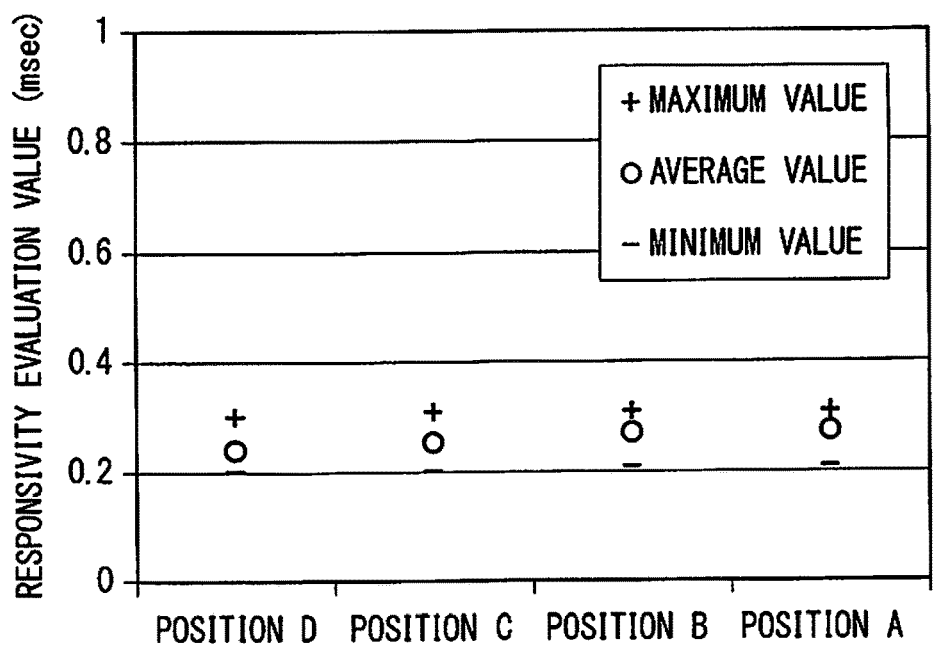
FIG. 15 is a diagram showing responsivity evaluation values of the gas sensor 1 disposed at inspection positions A to D, which are obtained by an inspection apparatus according to Comparative Example 3.
Figure 17:
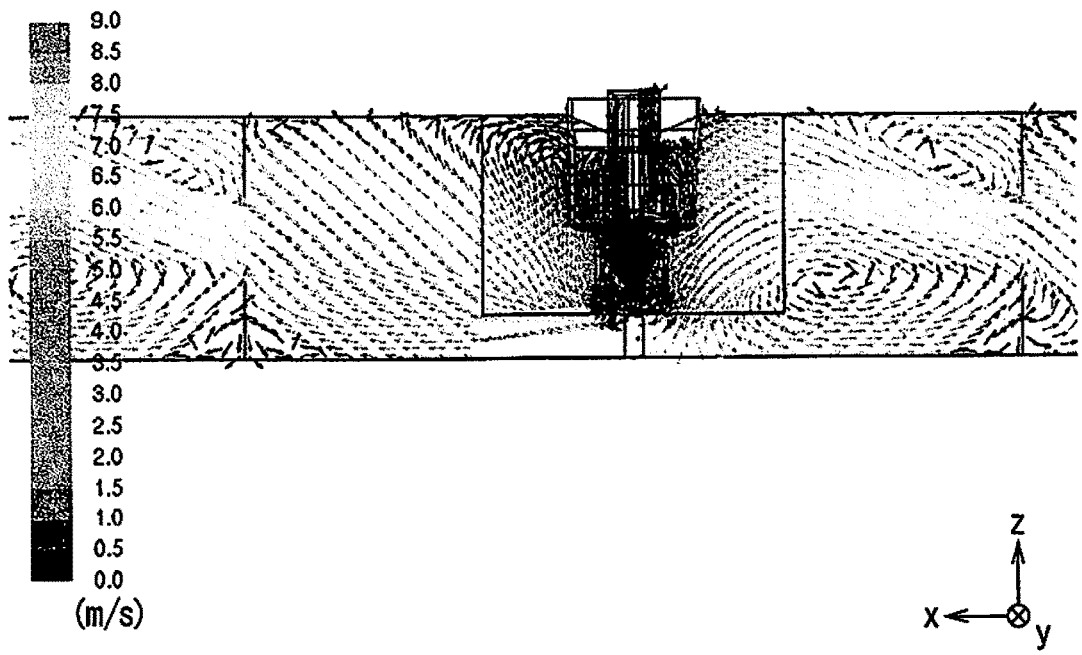
FIG. 17 is a vector diagram of flow speed distribution of a gas for inspection at the inspection position A.
Figure 18:
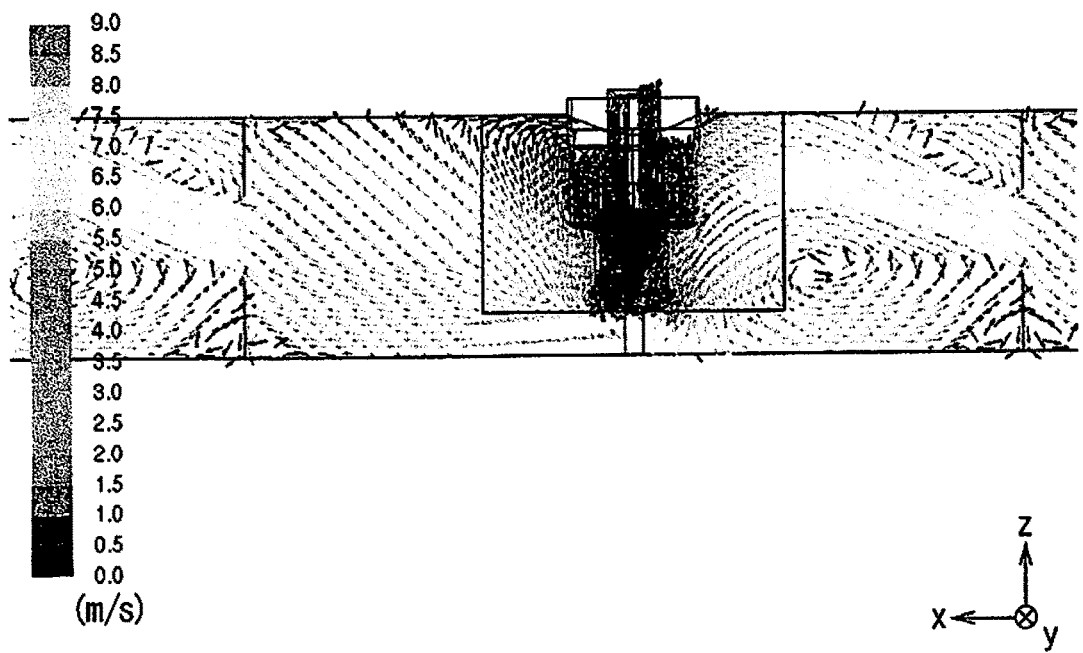
FIG. 18 is a vector diagram of flow speed distribution of a gas for inspection at the inspection position B.
Figure 19:
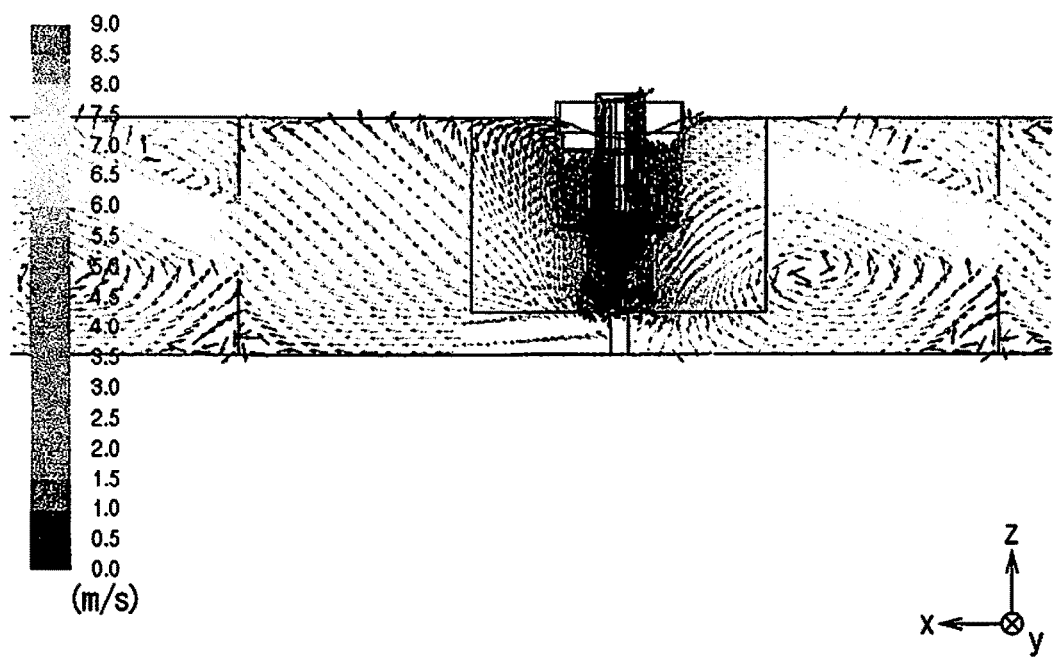
FIG. 19 is a vector diagram of flow speed distribution of a gas for inspection at the inspection position C.
Figure 20:
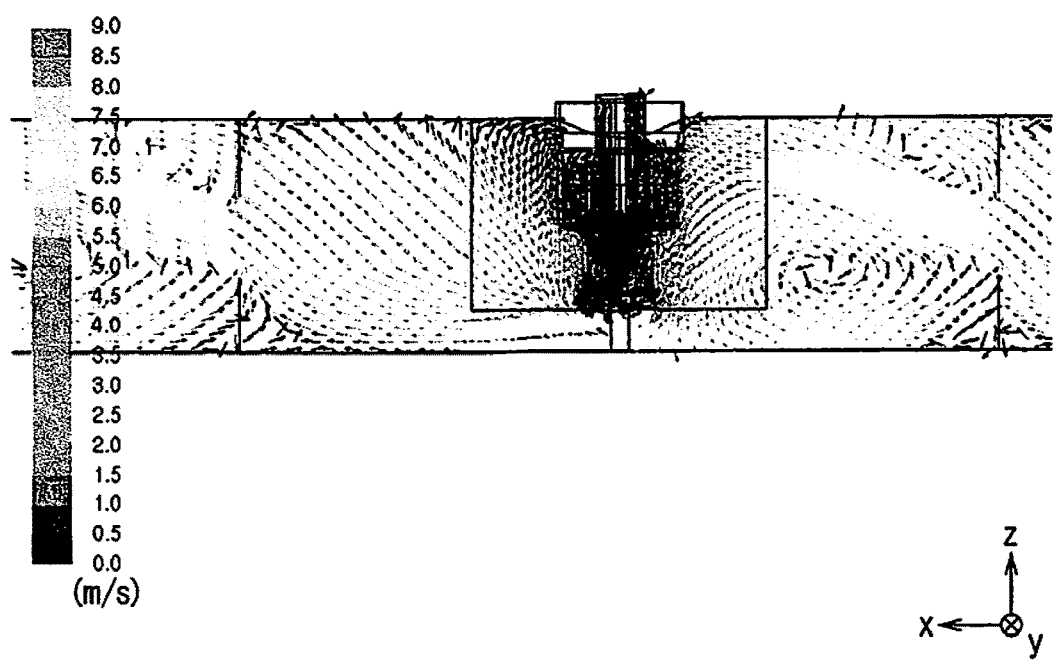
FIG. 20 is a vector diagram of flow speed distribution of a gas for inspection at the inspection position D.

In FIG. 15 showing a result of Comparative Example 3, the average value of the responsivity evaluation value has a small difference among the inspection positions, and the fluctuation thereof is about 0.1 msec irrespective of the inspection positions.

The above-described results indicate that the configuration according to Example 1, in which the straightening plate 1070 is provided in the chamber 1001A of the inspection apparatus 1000, is more effective in reducing the fluctuation of the responsivity evaluation value among the inspection positions while achieving the accuracy of the responsivity evaluation value, than the configuration according to Comparative Examples 1 to 3, in which the straightening plates 1071 to 1073 are provided.

In comparison of FIG. 12 showing the result of Example 1 and FIG. 16 showing the result of Example 2, the fluctuation of the responsivity evaluation value at the inspection position A was larger than that at the other inspection positions in Example 1 as described above, but, in Example 2, the average value of the responsivity evaluation value was substantially constant at about 0.3 msec irrespective of the inspection positions, and, the fluctuation of the responsivity evaluation value was substantially zero at all inspection positions.

The above-described results indicate that the inspection apparatus 1000 according to Example 2 including the chamber 1001B provided with the dummy pipe unit 2010 upstream of the inspection pipe unit 1010A that provides the inspection position A in the chamber 1001A is more effective in reducing the fluctuation of the responsivity evaluation value among the inspection positions than the configuration according to Example 1.

(Flow Speed Distribution Simulation)

The flow speed distribution of a gas for inspection inside the chamber 1001B when responsivity evaluation is performed on the inspection apparatus 1000 according to Example 2 was simulated. FIGS. 17 to 20 are vector diagrams illustrating the flow speed distribution of the gas for inspection at the inspection positions A to D, respectively. This simulation was performed under a condition that a bottom part of the outer protection cover 2 as a lower end part of the entire gas sensor 1 is in contact with the temperature sensor disposed in the temperature sensor disposing part 1040. The bottom part and the temperature sensor are separated from each other by an appropriate distance when the inspection is actually performed in the inspection apparatus 1000, but the above-described condition is intended to generate the flow of the gas for inspection inside the outer protection cover 2 and the inner protection cover 3 as much as possible.

In FIGS. 17 to 20, the flow speed of the gas for inspection near the gas sensor 1 is 1.0 m/s or lower at the inspection positions A to D, indicating that the gas flow speed distribution has almost no difference among the inspection positions A to D. In other words, in the configuration in which the straightening plate 1070 is provided upstream of each of the inspection positions and the dummy pipe unit 2010 is further provided upstream of the inspection pipe unit 1010A that provides the inspection position A, uniformity of the gas flow speed distribution is achieved inside the outer protection cover 2 and the inner protection cover 3 of the gas sensor 1 irrespective of the inspection positions. This suggests, together with the result of the responsivity evaluation according to Example 2 described above, that the uniformity of the gas flow speed distribution is effective in reducing the fluctuation of the responsivity evaluation value among the inspection positions.

While the invention has been shown and described in detail, the foregoing description is in all aspects illustrative and not restrictive. It is therefore understood that numerous modifications and variations can be devised without departing from the scope of the invention.

What is claimed is:

1. An apparatus configured to inspect responsivity of a gas sensor, said apparatus comprising:
    a chamber including one gas flow path,
    wherein said chamber includes a plurality of inspection pipe units, each including a cylindrical gas flowing part having an identical diameter, wherein the plurality of inspection pipe units are joined with each other from an upstream side so that the respective gas flowing parts are coaxially disposed forming said one gas flow path;
    a plurality of inspected sensor disposing parts that are provided halfway through said one gas flow path at equal intervals in an extending direction of said one gas flow path and in each of which a gas sensor to be inspected is disposed;
    a plurality of straightening plates provided on positions upstream of each of said inspected sensor disposing parts on said one gas flow path, each of said positions separated at a constant distance from the corresponding inspected sensor disposing parts,
    wherein:
    said straightening plates each include a rectangular opening orthogonal to said one gas flow path and open to said one gas flow path,
    when said one gas flow path extends in one direction in a horizontal plane, said rectangular opening has a longitudinal direction along a direction orthogonal to said one direction in the horizontal plane,
    a width of said rectangular opening is set to be same as a diameter of said one gas flow path, and a height of said rectangular opening is set to be smaller than said width, and
    said apparatus is configured to inspect said responsivity of said gas sensor by passing a gas for inspection through said one gas flow path when said gas sensor to be inspected is disposed at each of said inspected sensor disposing parts; and
    a dummy sensor disposing part provided halfway through said one gas flow path and upstream of an inspected sensor disposing part on a most upstream side among said inspected sensor disposing parts,
    wherein:

an interval between said dummy sensor disposing part and said inspected sensor disposing part on said most upstream side is same as an interval between said inspected sensor disposing parts, a straightening plate same as said straightening plates is provided on a position upstream of said dummy sensor disposing part on said one gas flow path, separated from said dummy sensor disposing part by said constant distance, and a dummy sensor having a structure same as a structure of said gas sensor to be inspected is disposed at said dummy sensor disposing part, at least when the responsivity of said gas sensor is inspected.

2. The inspection apparatus for a gas sensor according to claim 1, wherein said gas sensor to be inspected includes:
  a sensor element including an oxygen ion conducting solid electrolyte as a main component, and
  a protection cover configured to cover at least a first end part that is an end part on a side where a gas inlet of said sensor element is provided, wherein:
  said protection cover comprises a plurality of through-holes through which a gas is allowed to flow, and
  when said responsivity is inspected, said gas sensor to be inspected is disposed at each of said inspected sensor disposing parts to allow said gas for inspection to reach said first end part of said sensor element through said through-holes.

3. The inspection apparatus for a gas sensor according to claim 2, wherein the number of said inspected sensor disposing parts is not larger than 10.

4. The inspection apparatus for a gas sensor according to claim 1, wherein the number of said inspected sensor disposing parts is not larger than 10.

5. The inspection apparatus for a gas sensor according to claim 1, wherein said gas sensor is a NOx sensor.

* * * * *